US009945865B2

(12) United States Patent
Andrew

(10) Patent No.: US 9,945,865 B2
(45) Date of Patent: Apr. 17, 2018

(54) POLYMER NANOCOMPOSITES FOR EARLY DIAGNOSIS OF DISEASES

(71) Applicant: UNIVERSITY OF FLORIDA RESEARCH FOUNDATION, INC., Gainesville, FL (US)

(72) Inventor: Jennifer Andrew, Gainesville, FL (US)

(73) Assignee: UNIVERSITY OF FLORIDA RESEARCH FOUNDATION, INC., Gainesville, FL (US)

( * ) Notice: Subject to any disclaimer, the term of this patent is extended or adjusted under 35 U.S.C. 154(b) by 0 days.

(21) Appl. No.: 14/778,287

(22) PCT Filed: Jan. 31, 2014

(86) PCT No.: PCT/US2014/014155
§ 371 (c)(1),
(2) Date: Sep. 18, 2015

(87) PCT Pub. No.: WO2014/149196
PCT Pub. Date: Sep. 25, 2014

(65) Prior Publication Data
US 2016/0282358 A1    Sep. 29, 2016

Related U.S. Application Data

(60) Provisional application No. 61/804,459, filed on Mar. 22, 2013.

(51) Int. Cl.
G01N 33/58      (2006.01)
C12Q 1/37       (2006.01)
G01N 33/574     (2006.01)
A61K 49/00      (2006.01)
A61K 47/48      (2006.01)

(52) U.S. Cl.
CPC ..... *G01N 33/588* (2013.01); *A61K 47/48338* (2013.01); *A61K 49/0067* (2013.01); *A61K 49/0073* (2013.01); *C12Q 1/37* (2013.01); *C12Y 304/24007* (2013.01); *C12Y 304/24024* (2013.01); *C12Y 304/24035* (2013.01); *G01N 33/57488* (2013.01); *G01N 33/587* (2013.01); *G01N 2333/96494* (2013.01)

(58) Field of Classification Search
CPC .......... A61K 49/0067; A61K 49/0073; G01N 33/587; G01N 33/588
See application file for complete search history.

(56) References Cited

U.S. PATENT DOCUMENTS

| 7,914,982 | B2 | 3/2011 | Melkonyan | |
|---|---|---|---|---|
| 7,943,569 | B2 | 5/2011 | Gemeinhart | |
| 2008/0226562 | A1* | 9/2008 | Groves | A61K 49/0002 424/9.6 |
| 2010/0260677 | A1 | 10/2010 | Bhatia | |
| 2010/0279421 | A1* | 11/2010 | Strano | B82Y 15/00 436/86 |
| 2011/0008443 | A1 | 1/2011 | Alsberg | |
| 2011/0104194 | A1 | 5/2011 | Laal | |
| 2011/0212463 | A1* | 9/2011 | Delouise | G01N 33/54306 435/7.1 |
| 2012/0093722 | A1 | 4/2012 | Deming | |
| 2013/0136697 | A1 | 5/2013 | Kannan | |
| 2014/0249216 | A1* | 9/2014 | Lin | A61K 31/16 514/488 |

FOREIGN PATENT DOCUMENTS

EP    1882939 A1    1/2008
KR    20110038215 A    4/2011

OTHER PUBLICATIONS

Liu et al. (J. Mater. Chem., 2012, 22, 512).*
Liu et al. "ZnO quantum dots-embedded collagen/polyanion composite hydrogels with integrated functions of degradation tracking/inhibition and gene delivery" J. Mater. Chem., 2012, 22, 512-519.
International Search Report for International Application No. PCT/US2014/014155; International Filing Date Jan. 31, 2014; Report dated May 20, 2014 (6 pages).
Singh et al. "Realizing the Clinical Potential of Cancer Nanotechnology by Minimizing Toxicologic and Targeted Delivery Concerns" Cancer Res; 72(22) Nov. 15, 2012 (7 pages).
Written Opinion for International Application No. PCT/US2014/014155; International Filing Date Jan. 31, 2014; Report dated May 20, 2014 (7 pages).

* cited by examiner

*Primary Examiner* — Anna Falkowitz
(74) *Attorney, Agent, or Firm* — Cantor Colburn LLP

(57) ABSTRACT

Disclosed herein is a composition comprising a crosslinked hydrogel; where the hydrogel comprises a polymer having a cleavable bond along a backbone of the polymer, along a substituent that undergoes crosslinking, or along the backbone of the polymer and along the substituent that undergoes crosslinking; where the cleavable bond is operative to be cleaved by an enzyme released in the body of a living being; and a semiconducting quantum dot that emits light in the visible portion of the electromagnetic spectrum.

11 Claims, 3 Drawing Sheets

POLYMER NANOCOMPOSITES FOR EARLY DIAGNOSIS OF DISEASES

CROSS REFERENCE TO RELATED APPLICATIONS

This application claims priority to International Application No. PCT/US14/014155 filed on Jan. 31, 2014 which claims the benefit of U.S. Application No. 61/804,459 filed on Mar. 22, 2013, which are both incorporated herein by reference in its entirety.

BACKGROUND

This disclosure is related to polymer nanocomposites for early diagnosis of diseases.

Lung cancer is the most frequent cancer worldwide for men, and second only to breast cancer for women and is the leading cause of cancer death worldwide. Yet, if cancer is detected at its earliest stages it is a treatable, if not curable disease. Likewise, tuberculosis (TB) is one of the world's major public health problems, with 14 million cases worldwide and 1.7 million deaths in 2009 alone, according to WHO estimates. Additionally, it is estimated that around 60% of TB patients seek care at remote health clinics that lack the infrastructure to perform appropriate diagnostic tests. Microscopy, culture, and nucleic acid amplification are the only tests with proven clinical reliability in diagnosing tuberculosis, however none of these methods can be readily implemented at a remote health clinic. In order to achieve effective global diagnosis and treatment it is desirable to develop a tuberculosis test that is as simple to operate as over-the-counter tests, such as those used for pregnancy detection.

It is therefore desirable, in the case of cancer, tuberculosis and other diseases to develop tests that can operate simply without any complications, be eliminated from the body without any complications after their utility is concluded, and that can be distributed over-the-counter with few simple instructions.

SUMMARY

Disclosed herein is a composition comprising a crosslinked hydrogel; where the hydrogel comprises a polymer having a cleavable bond along a backbone of the polymer, along a substituent that undergoes crosslinking, or along the backbone of the polymer and along the substituent that undergoes crosslinking; where the cleavable bond is operative to be cleaved by an enzyme or biomarker released in the body of a living being; and a detectable nanoparticle that is optically or magnetically detectable.

Disclosed herein too is a method comprising inhaling, injecting or administering orally a composition comprising a crosslinked hydrogel; where the hydrogel comprises a polymer having a cleavable bond along a backbone of the polymer, along a substituent that undergoes crosslinking, or along the backbone of the polymer and along the substituent that undergoes crosslinking; where the cleavable bond is operative to be cleaved by an enzyme released in the body of a living being; and a detectable nanoparticle that is optically or magnetically detectable; cleaving the cleavable bond; releasing quantum dots from the body; and collecting the quantum dots.

DETAILED DESCRIPTION

Figure 1:
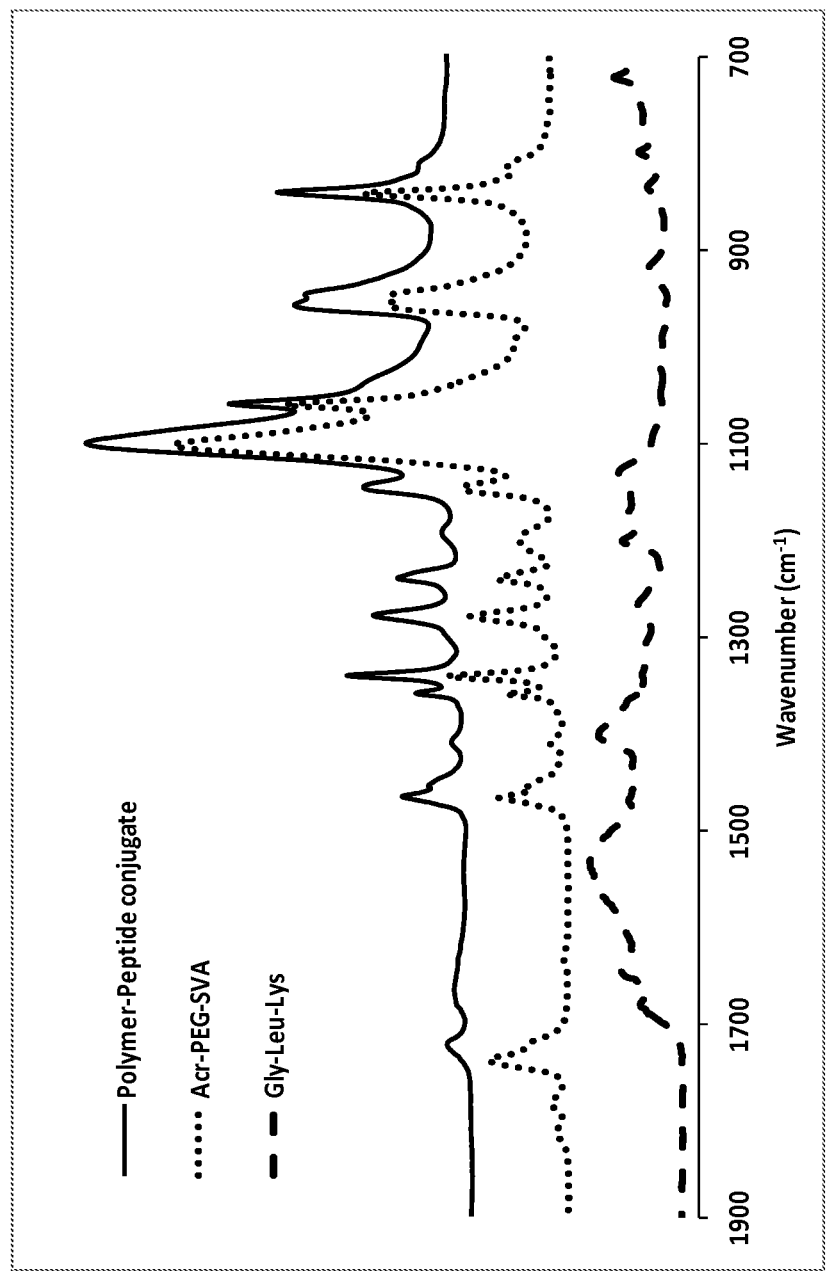
FIG. 1 is a plot showing a Fourier transform infrared spectra of the Gly-Leu-Lys peptide (dotted line), the Acr-PEG-SVA precursor (dashed line) and the Acr-PEG-peptide-PEG-Acr conjugate (black line)

Disclosed herein is a composition that can be used in a simple test for detecting diseases that can sometimes be debilitating or even fatal. Examples of such diseases are tuberculosis, cancers (e.g., lung cancer, pancreatic cancer, liver cancer, esophageal cancer, and the like), HIV/AIDS, and the like. The composition comprises an enzymatically degradable hydrogel that is loaded with a particular identifier (also termed a marker) for detection of a particular disease. The enzymatically degradable hydrogel comprises a water soluble polymer that has a polymer backbone or a substituent that comprises an enzymatically cleavable linker. The substituent is preferably one that contains a crosslinkable moiety that can crosslink one hydrogel polymer chain with another hydrogel polymer chain. The enzymatic cleavable linker is preferably a peptide linker. Peptide linkers are short chains composed of amino acids that are linked by peptide bonds. The peptide linker will be chosen such that the selection and order of the amino acids is recognized and cleaved by a disease biomarker. The amount of peptide linker can be varied from a maximum of 1 per polymer chain or less, specifically 0.5 per polymer chain, and the peptide linker concentration can be used to tune the degradation rate of the polymer. The enzymatically cleavable peptide linker will break down in the presence of enzymes that that are generated when a patient contracts a particular disease. The breakdown of the hydrogel permits the release of the marker, which is then detected in effluents that are ejected from the body of a patient, thus indicating that the patient has the particular disease.

Hydrogels are formed by crosslinking hydrophilic polymer chains—through physical, ionic or covalent interactions. It is desirable for the hydrogels to be non-toxic towards the bodies of living beings. The hydrogels have an enzymatically cleavable peptide linker disposed in the chain backbone, as a substituent off of the chain backbone, or both in the chain backbone and as a substituent off of the chain backbone. Hydrogels are available naturally or can be synthetically manufactured. Examples of naturally available hydrogels are xanthan gum, gum arabic, guar gum, locust bean gum, cellulose derivatives such as carboxymethyl cellulose, alginate and starch. Examples of synthetically manufactured hydrogels are polyvinyl alcohol, polyacrylamides, polyalkylacrylamides (e.g., poly(N-isopropylacrylamide)), polyalkylene glycols, polyethylene glycol, polypropylene glycol, poly(2-oxazoline), polyethylenimine, poly(acrylic acid), and polyelectrolytes (e.g., polystyrenesulfonic acid), or the like, or a combination comprising at least one of the foregoing hydrogels. The hydrogels are crosslinked.

The hydrogels may be copolymerized with other polymers that are not hydrogels, but that are also not toxic to the body of living beings. These other polymers are organic polymers that can be biodegradable polymers or non-biodegradable polymers. These non-hydrogel organic polymers can be thermoplastic or thermosetting polymers. The thermoplastic or thermosetting polymers can an oligomer, a homopolymer, or a copolymer which may be alternating, block, random or graft.

Examples of such biodegradable polymers polylactic-glycolic acid (PLGA), poly-caprolactone (PCL), copolymers of polylactic-glycolic acid and poly-caprolactone (PCL-PLGA copolymer), polyhydroxy-butyrate-valerate (PHBV), polyorthoester (POE), polyethylene oxide-butylene terephthalate (PEO-PBTP), poly-D,L-lactic acid-p-dioxanone-polyethylene glycol block copolymer (PLA-DX-PEG), or the like, or combinations comprising at least one of the foregoing biodegradable polymers.

Examples of the non-thermoplastic polymers are polyacetals, polyolefins, polycarbonates, polystyrenes, polyesters, polyamides, polyamideimides, polyarylates, polyarylsulfones, polyethersulfones, polyphenylene sulfides, polyvinyl chlorides, polysulfones, polyimides, polyetherimides, polytetrafluoroethylenes, polyetherketones, polyether etherketones, polyether ketone ketones, polybenzoxazoles, polyphthalides, polyacetals, polyanhydrides, polyvinyl ethers, polyvinyl thioethers, polyvinyl ketones, polyvinyl halides, polyvinyl nitriles, polyvinyl esters, polysulfonates, polysulfides, polythioesters, polysulfones, polysulfonamides, polyureas, polyphosphazenes, polysilazanes, polyurethane, perfluoroalkoxyethylene, polychlorotrifluoroethylene, polyvinylidene fluoride, or the like, or a combination comprising at least one of the foregoing thermoplastic polymers.

Examples of thermosetting polymers include epoxy polymers, unsaturated polyester polymers, polyimide polymers, bismaleimide polymers, bismaleimide triazine polymers, cyanate ester polymers, vinyl polymers, benzoxazine polymers, benzocyclobutene polymers, acrylics, alkyds, phenol-formaldehyde polymers, novolacs, resoles, melamine-formaldehyde polymers, urea-formaldehyde polymers, hydroxymethylfurans, isocyanates, diallyl phthalate, triallyl cyanurate, triallyl isocyanurate, unsaturated polyesterimides, or the like, or a combination comprising at least one of the foregoing thermosetting polymers.

When hydrogel polymers and non-hydrogel polymers are used in the composition, the hydrogel polymer are generally used in amounts of 50 to 95, preferably 55 to 85, and more preferably 75 to 80 weight percent based on the total weight of the polymer used in the composition. The non-hydrogel polymer may be used in amounts of 5 to 50, preferably 15 to 45, and more preferably 20 to 25 weight percent based on the total weight of the polymer used in the composition. In an embodiment, the non-hydrogel polymers may be used to coat the identifier before incorporating the polymer coated identifier into the hydrogel.

The hydrogel is present in the form of particles. In one embodiment, the particles are inhalable and can be present in the form of an aerosol that can be inhaled. In another embodiment, the particles can be ingested in the form of a water soluble capsule that can be swallowed. In yet another embodiment, the particles can be attached to a substrate that is present in a water soluble capsule, where the particles can be released from the substrate gradually over a period of time after the capsule has been dissolved.

The particles are generally available in sizes of 20 nanometers to 500 micrometers, preferably 50 nanometers to 200 micrometers, preferably 100 nanometers to 10 micrometers and more preferably 200 nanometers to 6 micrometers.

As detailed above, the hydrogel contains an identifier. The identifier is released upon degradation of the hydrogel by a particular enzyme that is released upon contacting a particular disease. The identifier is collected along with effluent (sweat, urine, feces, tears, and the like) from the body and its presence in the effluent is indicative of the disease that promotes the release of the particular enzyme. For example, matrix metalloproteinase-9 (MMP-9) and MMP-2 enzymes are overexpressed in lung cancer. The presence of MMP-2 or 9 will cause bond cleavage or degradation of the hydrogel, thus releasing the identifier, which is collected and analyzed. The presence of the identifier indicates that the patient has lung cancer.

It is desirable to use identifiers that are not damaging to the body of living beings, that do not agglomerate in any part of the body of living beings (i.e., they do not attach preferentially to any part of the body upon being released from the hydrogel) and that can be easily detected upon release from the human body. The identifier is a nanoparticle that is optically detectable or magnetically detectable.

Materials that can emit detectable radiation in the visible wavelength region (390 to 700 nanometers) are desirable for use as identifiers. Examples of identifiers are semiconducting quantum dots. The quantum dots have a diameter of 1 to 5 nanometers and can be a Group II-VI compound, a Group II-V compound, a Group III-VI compound, a Group III-V compound, a Group IV-VI compound, a Group I-III-VI compound, a Group II-IV-VI compound, or a Group II-IV-V compound. More preferably, the one-dimensional nanoparticle may be selected from the group consisting of Si, Ge, Pb, SiGe, ZnS, ZnSe, ZnTe, CdS, CdSe, CdTe, HgS, HgSe, HgTe, AlN, AlP, AlAs, AlSb, GaN, GaP, GaAs, GaSb, GaSe, InN, InP, InAs, InSb, TlN, TlP, TlAs, TlSb, PbS, PbSe, PbTe, or the like, or a combination comprising at least one of the foregoing semiconductors. In an exemplary embodiment, the one-dimensional nanoparticle comprises Si.

The quantum dots can be present in the composition in an amount of 0.5 to 15, preferably 1 to 14, and more preferably 1.5 to 5.0 wt %, based on the total weight of the composition.

In one embodiment, in one method of manufacturing the composition, the hydrogel is blended with the quantum dots and other ingredients such as additives, fillers, antibacterial agents, antipyretic agents, anti-inflammatory agents, initiators, crosslinking agents, accelerators, and the like. Water may be used during the blending lower the process viscosity. The water may be removed after the processing.

The hydrogel together with quantum dots may generally be processed in several different ways such as, melt blending, solution blending, or the like, or combinations comprising at least one of the foregoing methods of blending. Melt blending of the composition involves the use of shear force, extensional force, compressive force, ultrasonic energy, electromagnetic energy, thermal energy or combinations comprising at least one of the foregoing forces or forms of energy and is conducted in processing equipment wherein the aforementioned forces or forms of energy are exerted by a single screw, multiple screws, intermeshing co-rotating or counter rotating screws, non-intermeshing co-rotating or counter rotating screws, reciprocating screws, screws with pins, screws with screens, barrels with pins, rolls, rams, helical rotors, or combinations comprising at least one of the foregoing.

Melt blending involving the aforementioned forces may be conducted in machines such as single or multiple screw extruders, Buss kneader, Henschel, helicones, Ross mixer, Banbury, roll mills, molding machines such as injection molding machines, vacuum forming machines, blow molding machine, or the like, or combinations comprising at least one of the foregoing machines.

In one embodiment, the hydrogel in powder form, pellet form, sheet form, or the like, may be first dry blended with the quantum dots in a Henschel or in a roll mill, prior to being fed into a melt blending device such as an extruder or Buss kneader. It may be desirable to introduce the quantum dots into the melt blending device in the form of a masterbatch. In such a process, the masterbatch may be introduced into the melt blending device (e.g., an extruder) downstream of the point where the hydrogel is introduced.

A melt blend is one where at least a portion of the hydrogel has reached a temperature greater than or equal to about the melting temperature, if the hydrogel resin is a semi-crystalline polymer, or the flow point (e.g., the glass transition temperature) if the hydrogel is an amorphous polymer during the blending process. A dry blend is one where the entire mass of hydrogel is at a temperature less than or equal to about the melting temperature if the resin is a semi-crystalline polymer, or at a temperature less than or equal to the flow point if the polymer is an amorphous polymer and where the hydrogel is substantially free of any liquid-like fluid during the blending process. A solution blend, as defined herein, is one where the hydrogel is suspended in a liquid-like fluid such as, for example, a solvent or a non-solvent during the blending process.

Solution blending may also be used to manufacture the composition. The solution blending may also use additional energy such as shear, compression, ultrasonic vibration, or the like, to promote homogenization of quantum dots with the hydrogel. In one embodiment, the hydrogel is suspended in a fluid (e.g., water, an alcohol, or the like) is introduced into an ultrasonic sonicator along with the quantum dots. The mixture may be solution blended by sonication for a time period effective to disperse the quantum dots into the hydrogel. The hydrogel with the quantum dots may then be dried, extruded and molded if desired. During the extrusion, the temperature of the hydrogel may be raised to facilitate the crosslinking to take place. The fluid that is used to swell the hydrogel may be removed during the extrusion process by using a vacuum on the extruder.

In one embodiment, the composition may be manufactured by inverse emulsion polymerization. The quantum dots are incorporated into the composition during hydrogel microparticle synthesis. Microparticles can also be prepared via other solution based processes, including microfabrication, precipitation polymerization, suspension polymerization, and emulsion polymerization.

In one method, in one manner of using the composition, the composition is ingested or inhaled by a living being. If the living being is suffering from an onset of the disease for which the hydrogel contains cleavable bonds, the enzymes released by the presence of the bacteria/virus will cause the cleavable bonds to degrade thus releasing the quantum dots, which immediately pass from the diseased part of the body to the urine or to one of the other effluents released by the body. The presence of the quantum dots in the effluent may be detected by light scattering, spectrometry, and the like.

This method is advantageous in that the mechanism of detection is delivered orally or via inhalation, without intrusive surgery or without exposure to techniques such as xrays, magnetic resonance imaging, and the like.

The composition and the method of manufacture is further detailed by the following non-limiting examples.

EXAMPLE

Figure 2:
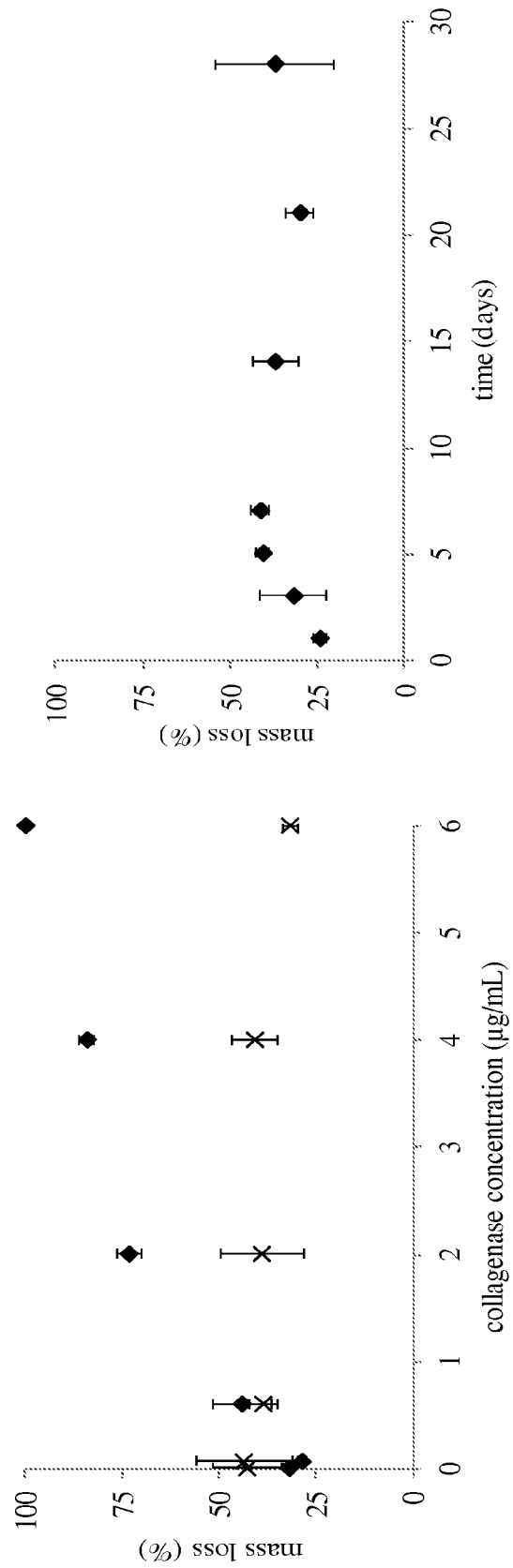
FIG. 2(A) shows degradation of PEG-peptide microparticles (black diamond) and PEGDA-10000 microparticles (x) with different concentrations of collagenase in solution, after 24 hours.
FIG. 2(B) shows long time degradation of the PEG-peptide microparticles in PBS.

This is an example to demonstrate the potential for detecting lung cancer or tuberculosis. In this study, an enzymatically degradable hydrogel poly(ethylene glycol) diacrylate is loaded with silicon (Si) quantum dots for lung cancer detection. An enzymatically cleavable peptide linker will be incorporated into the polymer backbone and will break down in the presence of matrix metalloproteinase-1, -2 or -9 (MMP-1, MMP-2, MMP-9) enzymes, which are overexpressed in lung cancer. The release of Si quantum dots from the gel will indicate a positive diagnosis. Shallow degradation profiles of the polymer-peptide hydrogels in the presence of a PBS solution indicate a slow breakdown of the hydrogels in the body with the absence of the MMP enzyme, which will prevent the release of quantum dots in the case of a negative diagnosis. Current research shows the peptide has been fully incorporated into the hydrogel, confirmed by FTIR (FIG. 1). Hydrogel swelling experiments reveal that crosslink density, mesh size and swelling ratios can be tuned by varying the concentration of peptide linkers in the hydrogel matrix. Degradation profiles of the hydrogel nanocomposite in a MMP-1 concentrated solution will be presented (FIG. 2).

Hydrogel microparticles were fabricated from poly(ethylene glycol) diacrylate macro-monomers consisting of a peptide encoded region, using an inverse emulsion synthesis method. Briefly, poly(ethylene glycol) diacrylate microparticles were obtained by emulsifying solutions of poly(ethylene glycol) diacrylate in water and oil, along with a photosensitive crosslinking agent. The resultant emulsification was placed under an ultraviolet (UV) lamp for two to thirty minutes to crosslink. The resultant particles were rinsed and freeze-dried. Incorporation of the peptide was verified using Fourier Transform Infrared Spectroscopy (FTIR). FIG. 1 shows the FTIR results reveal incorporation of the peptide into the polymer backbone. To determine the degradation properties of these microparticles 3-6 milligrams of the particles were dispersed in an MMP-1 solution in a TESCA buffer (50 mM of N-Tris(hydroxymethyl)-methyl-2-aminoethanesulfonic acid, 0.36 mM of calcium chloride $CaCl_2$, pH=7.4) in a 24-well plate. It was then incubated at 37° C. under a slight agitation for 24 hours. The remaining particles were then rinsed 3 times with DI water, and finally freeze dried, weighed and observed by scanning electron microscopy. The results from this degradation experiment are shown in FIG. 2. FIG. 2a compares the degradation of the hydrogel microparticles at concentrations between 0-6 ug/mL of MMP-1 (collagenase) compared with hydrogels composed of a similar molecular weight PEGDA, with no peptide encoded region. The peptide conjugated hydrogels show considerable degradation for MMP-1 concentrations greater than 2 ug/mL. At MMP-1 concentrations above 6 ug/mL complete degradation occurs for the peptide-conjugated hydrogels. However, it is important that while the peptide-encoded hydrogel degrades in the presence of MMP-1 that it does not degrade in the absence in MMP-1. FIG. 2b, reveals that after 30 days of incubation at 37° C. in PBS in the absence of the enzyme that considerable release does not occur.

Figure 3:
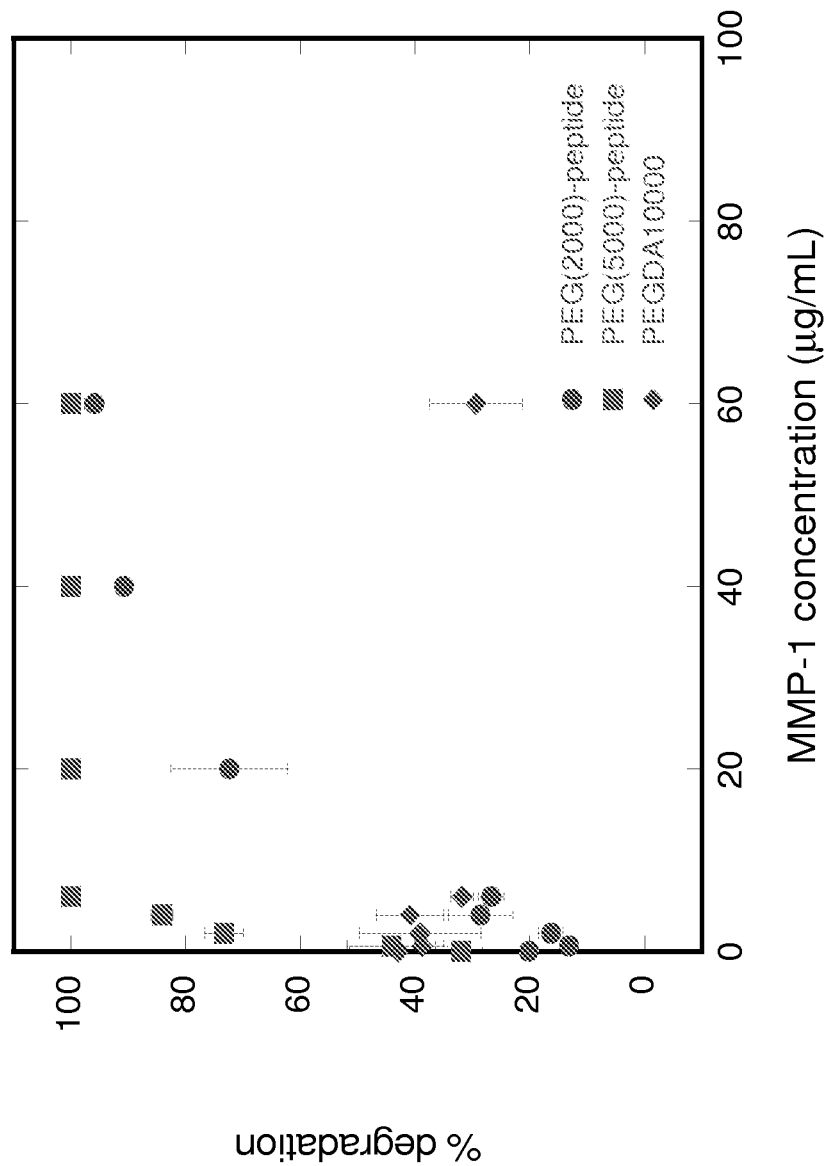
FIG. 3 is a plot showing the degradation profile of peptide-encoded gels synthesized from a 2000 and 5000 g/mol PEG precursor and a PEGDA 10,000 g/mol gel with no peptide incorporated for control in varying concentrations of MMP-1. All degradation experiments were performed with incubation for 24 hours with the enzyme.

Additionally, the degradation rate of the polymer can be tuned by varying its physical characteristics. FIG. 3 shows the results of peptide encoded hydrogels fabricated with differing mesh sizes. These hydrogels were synthesized from PEG precursors with a molecular weight of 2000 and 5000 g/mol. Due to the larger mesh size in the gels fabricated from the 5000 g/mol SVA-PEG-ACL they undergo faster degradation due to enhanced enzyme diffusion.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A composition comprising:
   a crosslinked hydrogel; where the hydrogel comprises a polymer having a cleavable bond along a backbone of the polymer, along a substituent that undergoes crosslinking, or along the backbone of the polymer and along the substituent that undergoes crosslinking; where the cleavable bond is operative to be cleaved by an enzyme released in the body of a living being; where the hydrogel comprises xanthan gum, gum arabic, guar gum, locust bean gum, cellulose derivatives, carboxymethyl cellulose, hydroxypropyl cellulose, alginate, starch, polyvinyl alcohol, polyacrylamide, poly (N-isopropylacrylamide), polyalkylene glycol, poly(2-oxazoline), polyethylenimine, polyethylene glycol, polypropylene glycol, poly(acrylic acid), polystyrenesulfonic acid, or a combination comprising at least one of the foregoing hydrogels; and
   a detectable nanoparticle that is optically or magnetically detectable; where the cleavable bond is a an enzymatically cleavable peptide linker.

2. The composition of claim 1, where the detectable nanoparticle is a semiconducting quantum dot that emits light in the visible portion of the electromagnetic spectrum.

3. The composition of claim 1, where the hydrogel is blended or copolymerized with a biodegradable polymer.

4. The composition of claim 1, where the hydrogel is blended or copolymerized with a thermoplastic polymer or a thermosetting polymer.

5. The composition of claim 2, where the quantum dots have a particle diameter of 1 to 5 nanometers.

6. The composition of claim 1, where the quantum dots can be a Group II-VI compound, a Group II-V compound, a Group III-VI compound, a Group III-V compound, a Group IV-VI compound, a Group compound, a Group II-IV-VI compound, or a Group II-IV-V compound.

7. The composition of claim 1, where the quantum dots are selected from the group consisting of Si, Ge, Pb, SiGe, ZnS, ZnSe, ZnTe, CdS, CdSe, CdTe, HgS, HgSe, HgTe, AlN, AlP, AlAs, AlSb, GaN, GaP, GaAs, GaSb, GaSe, InN, InP, InAs, InSb, TlN, TlP, TlAs, TlSb, PbS, PbSe, PbTe, or a combination thereof.

8. The composition of claim 2, where the quantum dot comprises silicon.

9. The composition of claim 1, where the composition is suspended in an aerosol.

10. A method comprising:
    inhaling, injecting or administering orally a composition comprising:
    a crosslinked hydrogel; where the hydrogel comprises a polymer having a cleavable bond along a backbone of the polymer, along a substituent that undergoes crosslinking, or along the backbone of the polymer and along the substituent that undergoes crosslinking; where the cleavable bond is operative to be cleaved by an enzyme released in the body of a living being; where the cleavable bond is an enzymatically cleavable peptide linker; and
    a detectable nanoparticle that is optically or magnetically detectable;
    cleaving the cleavable bond;
    releasing quantum dots from the body; and
    collecting the quantum dots.

11. The method of claim 9, further comprising correlating the number of detectable nanoparticles with a particular disease.

* * * * *